US011627894B2

(12) United States Patent
Schmelzeisen-Redeker et al.

(10) Patent No.: US 11,627,894 B2
(45) Date of Patent: Apr. 18, 2023

(54) METHOD AND A DEVICE FOR DETERMINING A BODY FLUID GLUCOSE LEVEL OF A PATIENT, AND A COMPUTER PROGRAM PRODUCT

(71) Applicant: Roche Diabetes Care, Inc., Indianapolis, IN (US)

(72) Inventors: Guenther Schmelzeisen-Redeker, Lorsch (DE); Nikolaus Schmitt, Heidelberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 315 days.

(21) Appl. No.: 15/325,518

(22) PCT Filed: Jul. 16, 2015

(86) PCT No.: PCT/EP2015/066321
§ 371 (c)(1),
(2) Date: Jan. 11, 2017

(87) PCT Pub. No.: WO2016/008997
PCT Pub. Date: Jan. 21, 2016

(65) Prior Publication Data
US 2017/0156647 A1 Jun. 8, 2017

(30) Foreign Application Priority Data
Jul. 17, 2014 (EP) ..................... 14177540

(51) Int. Cl.
*A61B 5/145* (2006.01)
*A61B 5/1495* (2006.01)

(52) U.S. Cl.
CPC ........ *A61B 5/14532* (2013.01); *A61B 5/1495* (2013.01); *A61B 5/14503* (2013.01); *A61B 2560/0223* (2013.01)

(58) Field of Classification Search
None
See application file for complete search history.

(56) References Cited

U.S. PATENT DOCUMENTS 6,326,160 B1  12/2001  Dunn et al.
6,424,847 B1   7/2002  Mastrototaro et al.
(Continued)

FOREIGN PATENT DOCUMENTS

EP        1154718 B1   11/2001
WO   WO-2012/084157 A1   6/2012

OTHER PUBLICATIONS

Zuping Tang et al: "Clinical Chemistry/ Drug Effects and Point-Of-Care Glucose Testing Effects of Drugs on Glucose Measurements with Handheld Glucose Meters and a Portable Glucose Analyzer", Jan. 1, 2000 (Jan. 1, 2000), pp. 75-86, XP055142817, Retrieved from the Internet: URL:http://ajcp.ascpjournals.org/content/113/1/75.full.pdf [retrieved on Sep. 25, 2014].
(Continued)

*Primary Examiner* — Matthew Kremer
(74) *Attorney, Agent, or Firm* — Harness, Dickey & Pierce, P.L.C.

(57) ABSTRACT

A method for determining a body fluid glucose level of a patient from a continuous signal of a glucose sensor element of a continuous body fluid glucose monitoring device in a data processing unit, comprising receiving measurement data representing a continuous sensor signal provided by a glucose sensor element of a continuous body fluid glucose monitoring device in the data processing unit, receiving calibration data representing a time-dependent zero-signal level of the glucose sensor element in the data processing unit, determining a body fluid glucose level by processing at least the measurement data and the calibration data in the data processing unit, the processing comprising subtraction of the time dependent zero-signal level from the continuous
(Continued)

sensor signal, and providing result data indicative of the continuous body fluid glucose level in the processing unit; and a system for determining a body fluid glucose level of a patient.

9 Claims, 10 Drawing Sheets

(56) References Cited

U.S. PATENT DOCUMENTS

| | | | | |
|---|---|---|---|---|
| H2246 H * | 8/2010 | Miller | ............... | G16H 50/50 |
| | | | | 600/347 |
| 8,589,106 B2 | 11/2013 | Engelhardt et al. | | |
| 2001/0016682 A1 * | 8/2001 | Berner | ............... | A61B 5/14532 |
| | | | | 600/345 |
| 2005/0143635 A1 * | 6/2005 | Kamath | ............. | A61B 5/14532 |
| | | | | 600/347 |
| 2007/0038053 A1 | 2/2007 | Berner et al. | | |
| 2007/0135696 A1 * | 6/2007 | Ward | ............... | A61B 5/14532 |
| | | | | 600/345 |
| 2010/0292932 A1 | 11/2010 | Won | | |
| 2011/0040163 A1 * | 2/2011 | Telson | ............... | A61B 5/14532 |
| | | | | 600/347 |
| 2012/0166126 A1 | 6/2012 | Engelhardt et al. | | |
| 2012/0191362 A1 | 7/2012 | Schmitt et al. | | |
| 2013/0297222 A1 | 11/2013 | Callicoat et al. | | |
| 2013/0338628 A1 | 12/2013 | Robertson et al. | | |
| 2014/0138261 A1 | 5/2014 | Colas | | |
| 2015/0198501 A1 * | 7/2015 | Rule | ............... | A61B 5/15087 |
| | | | | 73/40.5 R |

OTHER PUBLICATIONS

International Search Report and Written Opinion of the ISA for PCT/EP2015/066321, ISA/EP, Rijswijk, NL, dated Sep. 17, 2015.
International Preliminary Report on Patentability with annexes for PCT/EP2015/066321, IPEA/EP, Berlin, dated Jun. 27, 2016.

* cited by examiner

METHOD AND A DEVICE FOR DETERMINING A BODY FLUID GLUCOSE LEVEL OF A PATIENT, AND A COMPUTER PROGRAM PRODUCT

CROSS-REFERENCE TO RELATED APPLICATIONS

This application is a 371 U.S. National Stage of International Application No. PCT/EP2015/066321, filed Jul. 16, 2015, which claims the benefit of and priority to European Patent Application No. 14177540.3, filed Jul. 17, 2014. The entire disclosures of the above applications are incorporated herein by reference.

The present disclosure refers to a method and a system for determining a body fluid glucose level a patient, and a computer program product.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. An insulin infusion pump is used as a therapeutic device to administer insulin to patients suffering from diabetes.

Diabetes mellitus, often referred to as diabetes, is a chronic condition in which a person has elevated glucose levels that result from defects in the body's ability to produce and/or use insulin. There are three main types of diabetes. Type 1 diabetes can be autoimmune, genetic, and/or environmental and usually strikes children and young adults. Type 2 diabetes accounts for 90 to 95% of diabetes cases and is linked to obesity and physical inactivity. Gestational diabetes is a form of glucose intolerance diagnosed during pregnancy and usually resolves spontaneously after delivery.

Diabetes is managed primarily by controlling the level of glucose in the blood. This level is dynamic and complex, and is affected by multiple factors including the amount and type of food consumed, and the amount of insulin (which mediates transport of glucose across cell membranes) in the blood. Glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information, such as blood glucose, is typically obtained from a capillary blood sample with a lancing device and is then measured with a handheld blood glucose meter. Interstitial glucose levels may be obtained from a continuous glucose sensor worn on the body.

A handheld device may receive patient information from a number of different sources, such as an insulin pump, a continuous glucose monitor, a computer program, user input, etc. In order to accurately utilize this information, the handheld device may need to calibrate the information received from these sources. For example, a handheld diabetes managing device may receive, from a continuous glucose monitor, raw data that is related to a glucose level of a patient. In order to make use of this raw data, the handheld diabetes managing device may need to be calibrated to correlate the received raw data with a measured blood glucose level of the patient. The accuracy of this calibration can affect the care and treatment of the patient.

Accordingly, there is a need for a method of calibrating a handheld diabetes managing device to determine an accurate estimated glucose level of a patient from data received from a continuous glucose monitor.

A variety of implantable electrochemical sensors has been proposed for detecting specific analysts or compositions in a patient's blood. For instance, glucose sensors are provided for use in obtaining an indication of blood glucose levels in a patient. Such readings are useful in monitoring a treatment regime which typically includes regular administration of insulin. Sensor signals provided by the sensor device are processed for determining the actual glucose level. In document EP 1 154 718 B1 use of a regression is proposed for correlating sensor signals representing measurement data with the actual blood glucose level.

Document U.S. Pat. No. 6,326,160 B1 discloses methods, systems, and devices for measuring the concentration of a target analyte presented in a biological system using a series of measurements obtained from a monitoring system and a Mixtures of Expert (MOE) algorithm. A method for measuring blood glucose in a subject is disclosed.

Document WO 2012/084157 A1 refers to a method for calibrating a handheld diabetes managing device based on data generated by a continuous glucose monitor. The method can include sampling a current of the continuous glucose monitor at a sampling interval over a time period to generate a plurality of current samples for the time period. The method can also include determining a mean, median and standard deviation of the plurality of current samples. The blood glucose level of the patient can be measured at a first time and a calibration equation that associates the plurality of current samples with the estimated glucose level of the patient based on the measured blood glucose level and the plurality of current samples can be determined when the standard deviation is less than a first threshold and an absolute value of a difference between the mean and median is less than a second threshold.

From document US 2012/0191362 A1 a method for operating measuring equipment for detecting an analyte in a bodily fluid by means of a continuously measuring blood glucose sensor is disclosed. A calibration method is carried out for the prospective calibration of the measuring equipment. At least three calibration points are detected in the calibration method, wherein each calibration point comprises a measurement signal form the measuring equipment and a reference value of an associated reference measurement. A plurality of possible slopes is established between the calibration points. At least on robust estimation method, using a formation of at least one median is used to determine a probable slope from the plurality of possible slopes. Furthermore, a measurement is carried out. During the measurement and using the probable slope, a concentration of the analyte in the bodily fluid is deduced from a measurement signal from the measuring equipment and the probable slope.

Document US 2007/0038053 A1 discloses a method for continuously measuring the concentration of target chemical analytes present in a biological system, and processing analyte-specific signals to obtain a measurement value that is closely correlated with the concentration of the target chemical analyte in the biological system. A raw measurement signal is processed in a conversion step in order to remove or correct for background information present in the signal. One such background signal is the baseline background. Baseline background interferes with the measurement of the analyte of interest. The baseline background may vary with time. In addition, electrochemically active interfering species and/or residual analyte can be resent in the device which will further interfere with measurement of the analyte of interest.

It has been considered that drug interference may potentially mask serious condition in the glucose level of a body fluid (Tang et al.: "Effects of Drugs on Glucose Measurements with handheld glucose meters and a portable glucose analyzer", Clinical Chemistry, 2000; 113, pages 75-86).

Document US 2013/0338628 A1 refers to a system including a processor and at least one memory configured to provide a response determinator. The response determinator may receive therapeutic and wellness data. Moreover, the response determinator may determine a response based on the received therapeutic and wellness data. The response may represent a reaction to a substance integrated with an ingestible event marker. The determined response may be provided to, for example, a therapy controller.

Document US 2013/0297222 A1 discloses methods and apparatus that permit an analyte concentration to be estimated from a measurement in the presence of compounds that interfere with the measurement.

Document US 2012/0191362 A1 discloses a method for operating measuring equipment for detecting an analyte in a bodily fluid by means of a continuously measuring blood glucose sensor. A calibration method is carried out for the prospective calibration of the measuring equipment.

Document US 2014/0138261 A1 refers to methods and systems to apply a plurality of test voltages to the test strip and measure a current transient output resulting from an electrochemical reaction in a test chamber of the test strip so that an estimated interferent value can be determined so that such interferent value can be used to correct the current transients at specific time points for more accurate glucose concentration determination.

Document US 2010/0292932 A1 refers to a method and an apparatus for estimating the features of target materials by using kinetic change information along time, when measuring the result of a chemical reaction between two materials, target materials and reactant, with an optical or electrochemical method.

SUMMARY

It is an object to provide a method and a system which provide for determining a body fluid glucose level of a patient from a continuous signal of a glucose sensor element of a continuous body fluid glucose monitoring device in an efficient and reliable manner.

A method and a system for determining a body fluid glucose level of a patient according to claims 1 and 9, respectively, are provided. Advantageous developments are disclosed in dependent claims.

According to an aspect, a method for determining a body fluid glucose level of a patient from a continuous signal of a glucose sensor element of a continuous body fluid glucose monitoring device in a data processing unit is provided. In the data processing unit measurement data are received, the measurement data are representing a continuous sensor signal provided by a glucose sensor element of a continuous body fluid glucose monitoring device in the data processing unit. The glucose sensor element may be configured for subcutaneous access, e.g. a measurement in the interstitium. Further, in the data processing unit calibration data are received, the calibration data representing a time-dependent zero-signal level of the glucose sensor element. A glucose level of a body fluid is determined by processing at least the measurement data and the calibration data in the data processing unit. In the step of processing the calibration data representing the time dependent zero-signal level are subtracted from the continuous sensor signal. Result data indicative of the glucose level of the body fluid are provided in the processing unit, which may be independent of an additional blood glucose reference.

According to another aspect, a system for determining a body fluid glucose level of a patient from a continuous signal of a glucose sensor element of a continuous body fluid glucose monitoring device is provided. The system comprising a data processing unit configured to receive measurement data representing a continuous sensor signal provided by a glucose sensor element of a continuous body fluid glucose monitoring device, receive calibration data representing a time-dependent zero-signal level of the glucose sensor element, determine a continuous glucose level of a body fluid by processing at least the measurement data and the calibration data in the data processing unit, the processing comprising subtraction of the time dependent zero-signal level from the continuous sensor signal, and provide result data indicative of the continuous glucose level of the body fluid in the processing unit.

The zero-signal level of the glucose sensor element being different from a zero output (an output which is zero—no detectable signal) may be indicative of a sensor output signal contribution in response to a substance other than glucose in the body fluid under investigation.

The body fluid under investigation may be, for example, one of interstitial fluid, blood, and urea.

The receiving the calibration data may comprise receiving calibration data representing a zero-signal level comprising an interferent signal contribution indicative of presence of at least one interferent in the body fluid for which the glucose level is determined. The glucose sensor element is responsive to the presence of the interferent (interfering substance) in the body fluid under investigation. In conclusion, with respect to the electrical output signal of the glucose sensor element there is signal interference affecting the zero-signal level.

The interferent signal contribution may be a time-dependent interferent signal contribution. As an alternative, the interferent signal contribution may not dependent on time which may also be referred to as a constant interferent signal contribution.

The receiving calibration data may comprise receiving calibration data representing a kinetic course of decomposition of an interferent in the body fluid for which the glucose level is determined. The kinetic course of decomposition may represent an (additional) interferent signal contribution with respect to its time dependence and/or its expected time-dependent signal height at the output of the glucose sensor element.

The receiving calibration data may comprise receiving an event starting input indicative of a starting time of the presence of the interferent in the body fluid for which the glucose level is determined. Together with the kinetic course of decomposition of the interferent this information may be used for calibrating the sensor signals received from the glucose sensor element.

In the method for determining the glucose level, the receiving calibration data may comprise generating a prompting signal for calibration data input. By the prompting signal the user may be requested to provide input of the calibration data.

The generating the prompting signal may comprise receiving a user selection input. For example, the user may select calibration data input from some external or internal storage medium.

The processing unit may be provided in one of a handheld body fluid glucose management device, and a continuous body fluid glucose measurement device. In some embodiments, the processing unit may be provided in one of a handheld blood glucose management device, a continuous blood glucose measurement device, a handheld interstitial fluid management device, and a continuous interstitial fluid glucose measurement device.

With respect to the system for determining the glucose level of a body fluid of a patient, the embodiments described above with reference to the method may apply accordingly.

According to another aspect, not necessarily to be combined with the method or the system for determining the body fluid glucose level of a patient, a method for determining a pharmacokinetic curve for an active substance or composition in a body fluid from a continuous sensor signal of a glucose sensor element of a continuous body fluid glucose monitoring device in a data processing unit may be provided. In the processing unit first measurement data are received, the first measurement data are representing a continuous sensor signal provided by a glucose sensor element of a continuous body fluid glucose monitoring device. The glucose sensor element may be configured for subcutaneous access. The glucose sensor element may be configured for interstitial fluid or blood measurement. In the data processing unit further data, for example, second measurement data are provided, the further data representing a sensor signal provided from a further body fluid glucose monitoring different from the continuous body fluid glucose monitoring device. The further body fluid glucose monitoring may also be from the continuous body fluid glucose monitoring type. The first measurement data and the further data are processed for determining a pharmacokinetic curve of an active substance or composition causing time-dependent signal interference for the first measurement data. The further data are not interfered by signal contribution of the active substance. Therefore, a pharmacokinetic curve can be determined from processing of the first measurement data and the further data. If the first measurement data and the further data represent the same glucose level of a patient, but measured independently, the pharmacokinetic curve may simply be determined by subtracting the further data from the first measurement data. Surprisingly, the measurements for determining body fluid glucose level may be used for determining kinetic behavior of an active substance or composition in the body fluid.

In general, the method may also be performed by using measured data from a sensor element providing signals indicative of another analyte, such as lactate, present in the body fluid under investigation. The body fluid may be, for example, one of interstitial fluid, blood, and urea. At least two independent sources for data (e.g. measurement with the active component present, and measurement with no presence of the active component) need to be analyzed. One or more steps of the method may be combined with the method or the system for determining the body fluid glucose level of a patient provided in the present disclosure. Also one or more steps of the method or the system for determining the body fluid glucose level of a patient may be combined with the method for determining a pharmacokinetic curve for an active substance or composition in a bodily fluid.

The data used in the method for determining the pharmacokinetic curve for an active substance or composition in a body fluid from the continuous sensor signal of the glucose sensor element of the continuous body fluid glucose monitoring at least in a part may be taken from a calibration process performed for the device. Different calibration methods may be applied, e.g. by comparing calibration with a constant offset and calibration with a calibrated offset.

DESCRIPTION OF EMBODIMENTS

Following, embodiments, by way of example, are described with reference to figures. In the figures show.

Figure 1:
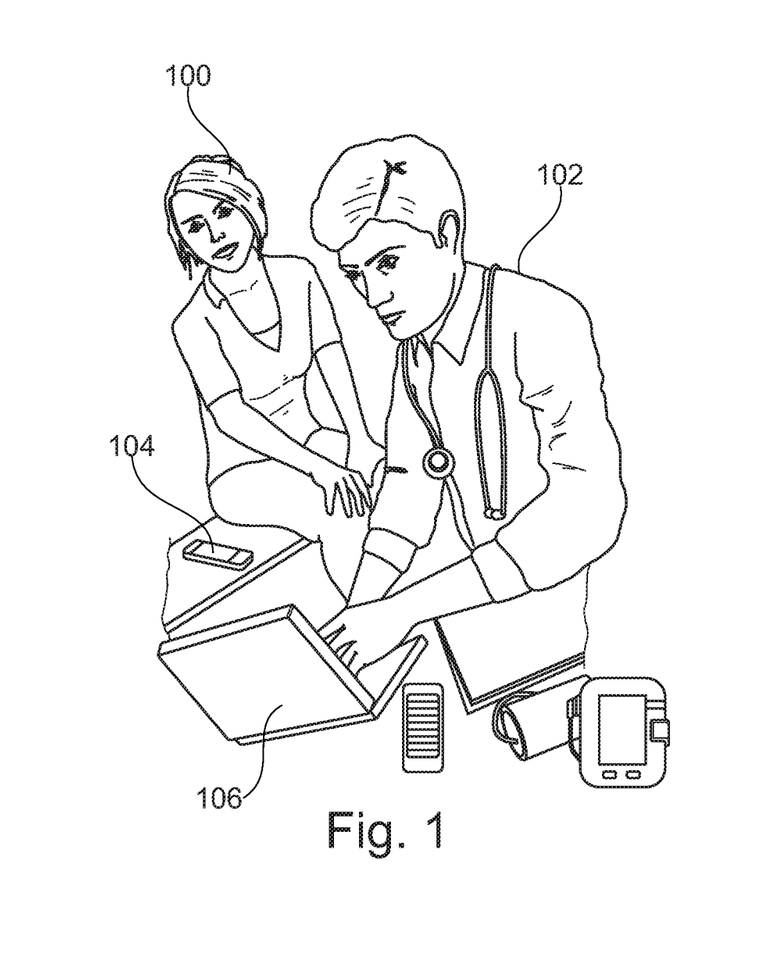
FIG. 1 a schematic representation of a patient and a treating clinician.

Referring now to FIG. 1, a person 100 with diabetes and a healthcare professional 101 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 101 a variety of patient data including blood glucose measurements, continuous glucose monitor data, amounts of insulin infused, amounts of food and beverages consumed, exercise schedules, and other lifestyle information. The clinician 101 can obtain additional patient data that includes measurements of HbA1C, cholesterol levels, triglycerides, blood pressure, and weight of the patient 100. The patient data can be recorded manually or electronically on a handheld diabetes managing device 102, a diabetes analysis software executed on a personal computer (PC) 106, and/or a web-based diabetes analysis site (not shown). The clinician 101 can analyze the patient data manually or electronically using the diabetes analysis software and/or the web-based diabetes analysis site. After analyzing the patient data and reviewing adherence of the patient 100 to previously prescribed therapy, the clinician 101 can decide whether to modify the therapy for the patient 100.

Figure 2:
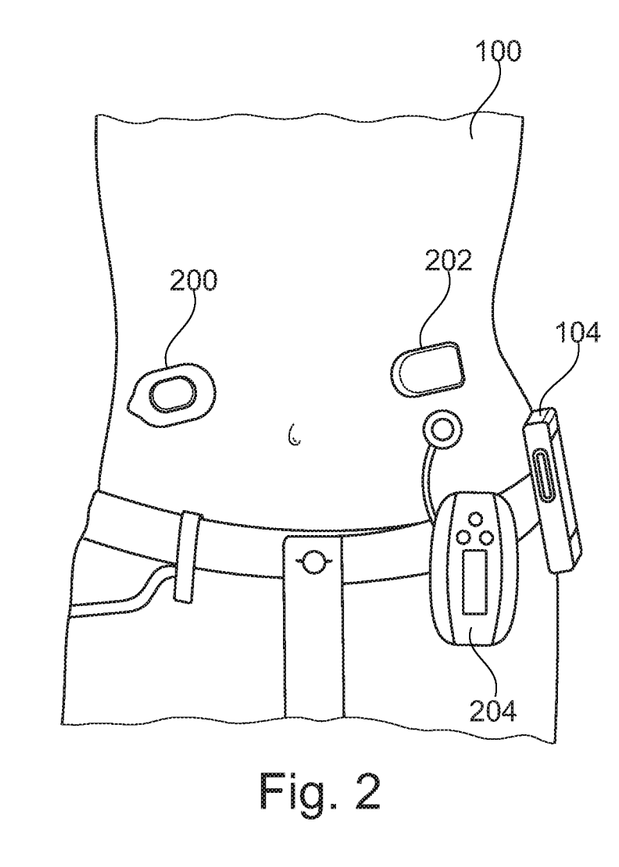
FIG. 2 a schematic representation of a patient with a continuous glucose monitor (CGM), ambulatory durable insulin infusion pump, ambulatory non-durable insulin infusion pump, and diabetes manager, FIG. 3 a schematic representation of a diabetes care system, FIG. 4 a functional block diagram of a diabetes manager, FIG. 5 a functional block diagram of a continuous glucose body fluid, FIG. 6 a block diagram of a method for determining a body fluid glucose level of a patient from continuously measured sensor signals of a glucose sensor element, and FIG. 7 graphical representation of time-dependent curves, and FIG. 8 a block diagram of a method for determining a body fluid glucose level of a patient from continuously measured sensor signals of a glucose sensor element.

Referring now to FIG. 2, the patient 100 can use a continuous glucose monitor (CGM) 200, an ambulatory durable insulin infusion pump 201 or an ambulatory non-durable insulin infusion pump 202 (collectively insulin pump 201 or 202), and the handheld diabetes managing device 102 (hereinafter the diabetes manager 102). The CGM 200 uses a subcutaneous sensor to sense and monitor the amount of glucose in the subcutaneous fluid of the patient 100 and communicates corresponding readings to the handheld diabetes managing device 102.

The diabetes manager 102 performs various tasks including measuring and recording blood glucose levels, determining an amount of insulin to be administered to the patient 100 via the insulin pump 201 or 202, receiving patient data via a user interface, archiving the patient data, etc. The diabetes manager 102 periodically receives readings from the CGM 200 indicating a glucose level in the subcutaneous fluid of the patient 100. The diabetes manager 102 transmits instructions to the insulin pump 201 or 202, which delivers insulin to the patient 100. Insulin can be delivered in the form of a bolus dose, which raises the amount of insulin in the blood of the patient 100 by a predetermined amount. Additionally, insulin can be delivered in a scheduled manner in the form of a basal dose, which maintains a predetermined insulin level in the blood of the patient 100.

Figure 3:
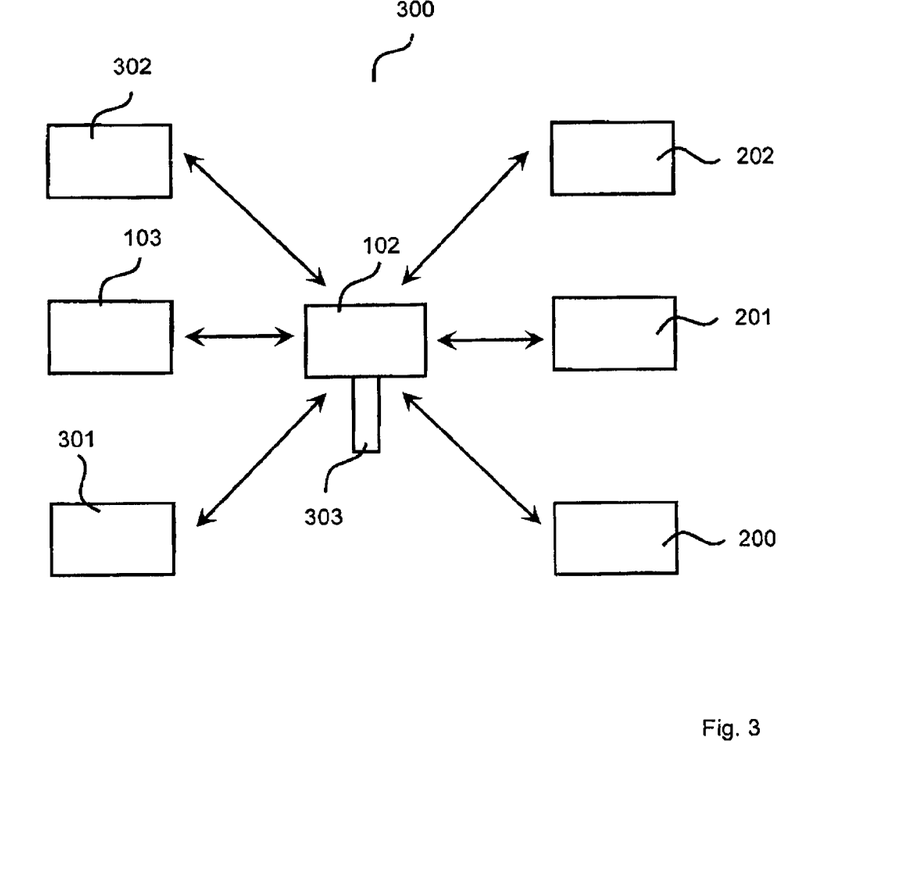

Referring now to FIG. 3, a diabetes management system 300 used by the patient 100 and the clinician 101 includes one or more of the following devices: the diabetes manager 102, the continuous glucose monitor (CGM) 200, the insulin pump 201 or 202, a mobile device 301, the diabetes analysis software on the PC 103, and other healthcare devices 302. The diabetes manager 102 is configured as a system hub and communicates with the devices of the diabetes management system 300. Alternatively, the insulin pump 202 or the mobile device 301 can serve as the system hub. Communication between the various devices in the diabetes management system 300 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 101 to exchange information.

The diabetes manager 102 can receive glucose readings from one or more sources (e.g., from the CGM 200). The CGM 200 continuously measures the glucose level of the patient 100. The CGM 200 periodically communicates the glucose level to the diabetes manager 102. The diabetes manager 102 and the CGM 200 communicate wirelessly using a proprietary wireless protocol.

Additionally, the diabetes manager 102 includes a blood glucose meter (BGM) and a port that communicates with the BGM (both not shown). The port can receive a blood glucose measurement strip 303. The patient 100 deposits a sample of blood or other bodily fluid on the blood glucose measurement strip 303. The BGM analyzes the sample and measures the blood glucose level in the sample. The blood glucose level measured from the sample and/or the blood glucose level read by the CGM 200 can be used to determine the amount of insulin to be administered to the patient 100.

The diabetes manager 102 communicates with the insulin pump 201 or 202. The insulin pump 201 or 202 can be configured to receive instructions from the diabetes manager 102 to deliver a predetermined amount of insulin to the patient 100. Additionally, the insulin pump 201 or 202 can receive other information including meal and/or exercise schedules of the patient 100. The insulin pump 201 or 202 can determine the amount of insulin to administer based on the additional information.

The insulin pump 201 or 202 can also communicate data to the diabetes manager 102. The data can include amounts of insulin delivered to the patient 100, corresponding times of delivery, and pump status. The diabetes manager 102 and the insulin pump 201 or 202 can communicate using a wireless communication protocol such as Bluetooth. Other wireless or wireline communication protocols can also be used.

In addition, the diabetes manager 102 can communicate with other healthcare devices 302. For example, the other healthcare devices 302 can include a blood pressure meter, a weight scale, a pedometer, a fingertip pulse oximeter, a thermometer, etc. The other healthcare devices 302 obtain and communicate personal health information of the patient 100 to the diabetes manager 102 through wireless, USB, or other interfaces. The other healthcare devices 302 use communication protocols compliant with ISO/IEEE 11073 extended using guidelines from Continual® Health Alliance. The diabetes manager 102 can communicate with the other healthcare devices 302 using interfaces including Bluetooth, USB, etc. Further, the devices of the diabetes management system 300 can communicate with each other via the diabetes manager 102.

The diabetes manager 102 can communicate with the PC 103 using Bluetooth, USB, or other interfaces. A diabetes management software running on the PC 103 includes an analyzer-configurator that stores configuration information of the devices of the diabetes management system 300. The configurator has a database to store configuration information of the diabetes manager 102 and the other devices. The configurator can communicate with users through standard web or computer screens in non-web applications. The configurator transmits user-approved configurations to the devices of the diabetes management system 300. The analyzer retrieves data from the diabetes manager 102, stores the data in a database, and outputs analysis results through standard web pages or computer screens in non-web based applications.

The diabetes manager 102 can communicate with the mobile device 301 using Bluetooth. The mobile device 301 can include a cellular phone, a PDA, or a pager. The diabetes manager 102 can send messages to an external network through the mobile device 301. The mobile device 301 can transmit messages to the external network based on requests received from the diabetes manager 102.

In some embodiments, the CGM 200 measures the level of glucose in the interstitial fluid of the patient 100 by sampling a current. The level of glucose in the interstitial fluid, and therefore the sampled current, is related to the glucose level of the patient 100. In order to accurately estimate the glucose level of the patient 100 based on the interstitial fluid glucose level measured by the CGM 200, the diabetes manager 102 can be periodically calibrated.

The diabetes manager 102 can be calibrated by determining a calibration equation based on at least one current sample and at least one blood glucose measurement. The current sampled by the CGM 200 and the blood glucose level of the patient 100 can be assumed to have a linear relationship within a normal measurement region of approximately 40 to 400 Milligrams per Deciliter. Based on this assumed linear relationship, the calibration equation can be a linear equation that associates one or more current samples with an estimated glucose level of the patient. After calibration, the diabetes manager 102 can determine an estimated glucose level of the patient 100 based on the calibration equation and the current sampled by the CGM 200.

Figure 4:
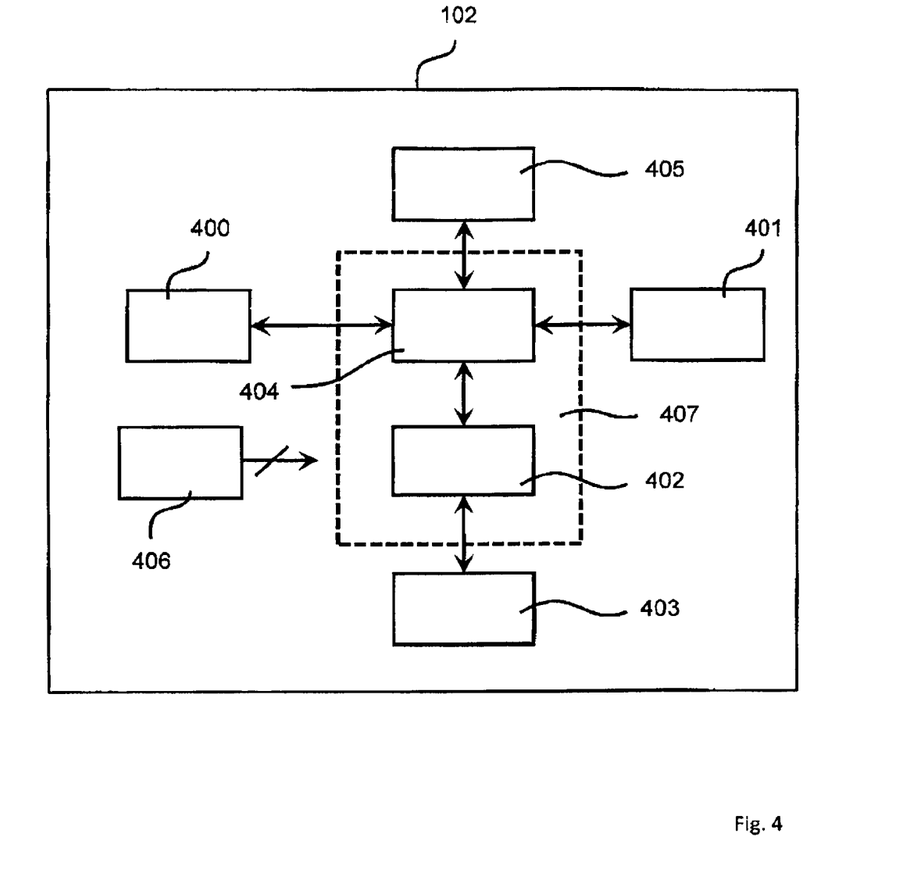

Referring now to FIG. 4, an exemplary diabetes manager 102 includes a blood glucose measuring (BGM) module 400, a communication module 401, a user interface module 402, user interfaces 403, a processing module 404, memory 405, and a power module 406. The user interface module 402 and the processing module 404 can be implemented by an application processing module 407. The BGM module 400 includes a blood glucose measuring engine that analyzes samples provided by the patient 100 on the blood glucose measurement strip 303 and that measures the amount of blood glucose in the samples. The communication module 401 can include multiple radios that communicate with different devices of the diabetes management system 300. The user interface module 402 connects the diabetes manager 102 to various user interfaces 403 that the patient 100 can use to interact with the diabetes manager 102. For example, the user interfaces 403 can include keys, switches, a display, a speaker, a microphone, a secure digital (SD) card port, and/or a USB port (all not shown).

The processing module 404 processes data received from the BGM module 400, the communication module 401, and the user interface module 402. The processing module 404 uses memory 405 for processing and storing data. The memory 405 can include volatile and non-volatile memory. The processing module 404 outputs data to and receives data from the user interfaces 403 via the user interface module 402. The processing module 404 outputs data to and receives data from the devices of the diabetes management system 300 via the communication module 401. The power module 406 supplies power to the components of the diabetes manager 102. The power module 406 can include a rechargeable battery or other source of power. The battery can be recharged, e.g., by using an adapter that plugs into a wall outlet and/or via a USB port on the diabetes manager 102.

Figure 5:
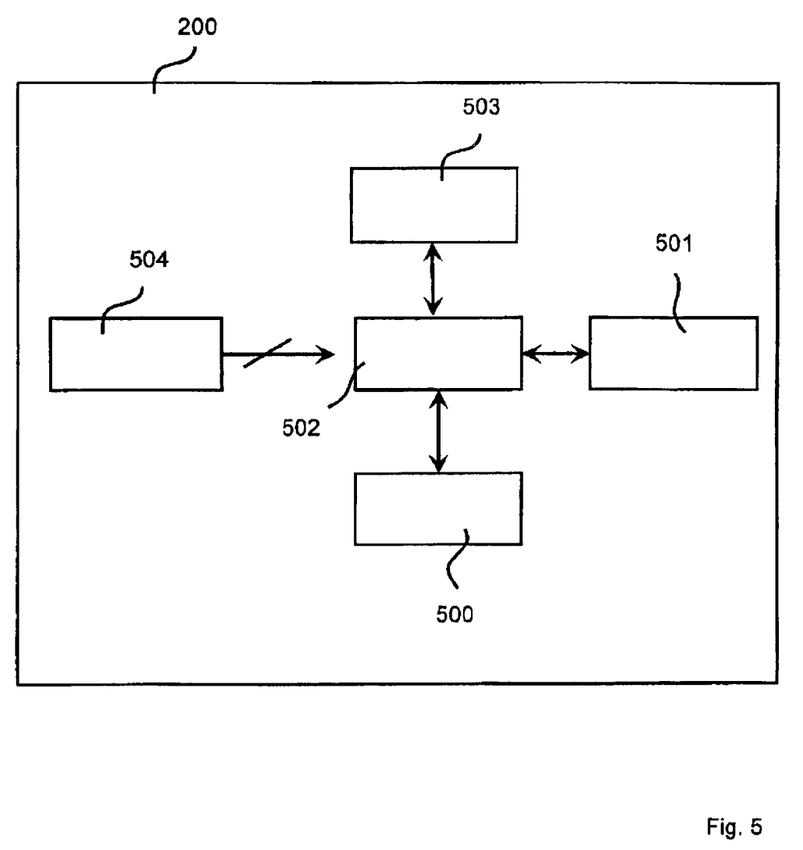

Referring now to FIG. 5, an exemplary continuous glucose monitor (CGM) 200 includes a sensor 500, a communication module 501, a processing module 502, memory 503, and a power module 504. The sensor 500 can monitor a condition of the patient 100 that is related to the glucose level of the patient 100. For example, the sensor 500, alone or in combination with processing module 502, can periodically sample a current value that corresponds to the level of glucose in the interstitial fluid of the patient 100. The communication module 501 can include one or more radios that communicate with different devices of the diabetes management system 300.

The processing module 502 processes data received from the sensor 500 and the communication module 501. The processing module 502 uses memory 503 for processing and storing data. The memory 503 can include volatile and nonvolatile memory. The processing module 502 outputs data to and receives data from the devices (for example, diabetes manager 102) of the diabetes management system 300 via the communication module 501. The power module 504 supplies power to the components of the CGM 200. In some embodiments, the power module 504 includes a battery or other source of power. The source of power may include a battery that can be recharged, e.g., by using an adapter that plugs into a wall outlet.

Figure 6:
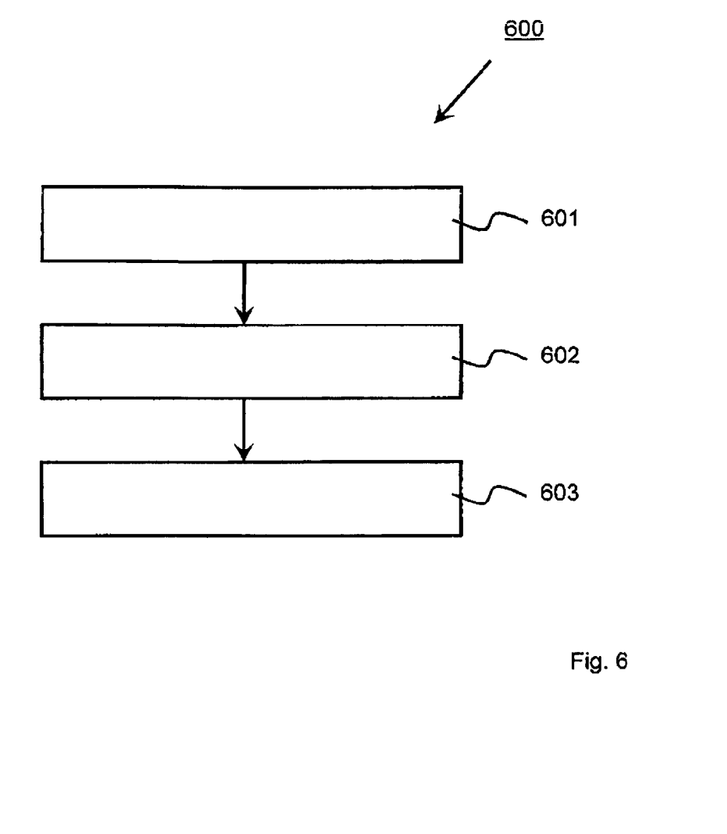

Referring to FIG. 6, an exemplary method 600 for determining a continuous body fluid glucose level of a patient is illustrated. The method 600 begins at step 601 where in a data processing unit measurement data are received. The data processing unit, for example, may be provided in the handheld diabetes management device 102 or the continuous glucose monitor 200. The processing module 404 or 502 may be provided with the data processing unit. The measurement data received are indicative of a continuous sensor signal provided by a glucose sensor element such as sensor 500.

In step 602 calibration data are received in the data processing unit, the calibration data are representing a time dependent zero-signal level of the glucose sensor element used for detecting the continuous sensor signal. The zero-signal level of the glucose sensor element is different from a zero output (an output which is actually zero; non-detectable signal) and may be indicative of a sensor output signal contribution in response to one or more active substances other than glucose in the bodily fluid (blood) under investigation. In step 603 a continuous blood glucose level is determined by processing at least the measurement data and the calibration data in the data processing unit, such processing comprising subtraction of the zero-signal level from the continuous sensor signal provided by the glucose sensor element. The data processing unit may synchronize the timing of the zero-signal level and the continuous sensor signal according to the start time of the interferent presence in the body. Sensor signal contributions caused by any substance different from glucose are deleted afterwards. Such signal processing may be considered as being (part of) a calibration.

The calibration data may represent a zero-signal level comprising an interferent signal contribution indicative of presence of at least one interferent in the body fluid for which the glucose level is determined. For example, the patient may have taken aspirin the time-dependent decomposition which may cause time-dependent sensor signal contribution. Information as to the time dependence of the decomposition of aspirin, for example, may be taken from C. Bogentoft, et al.: Influence of Food on the Absorption of Acetylsalicylic Acid from Enteric-Coated Dosage Forms, Europ. J. din. Pharmacol. 14, 351-355 (1978).

The glucose sensor element is responsive to the presence of the interferent (interfering substance) in the body fluid under investigation, e.g. blood or interstitial fluid. In conclusion, with respect to the electrical output signal of the glucose sensor element there is signal interference affecting the zero-signal level.

Figure 7A:
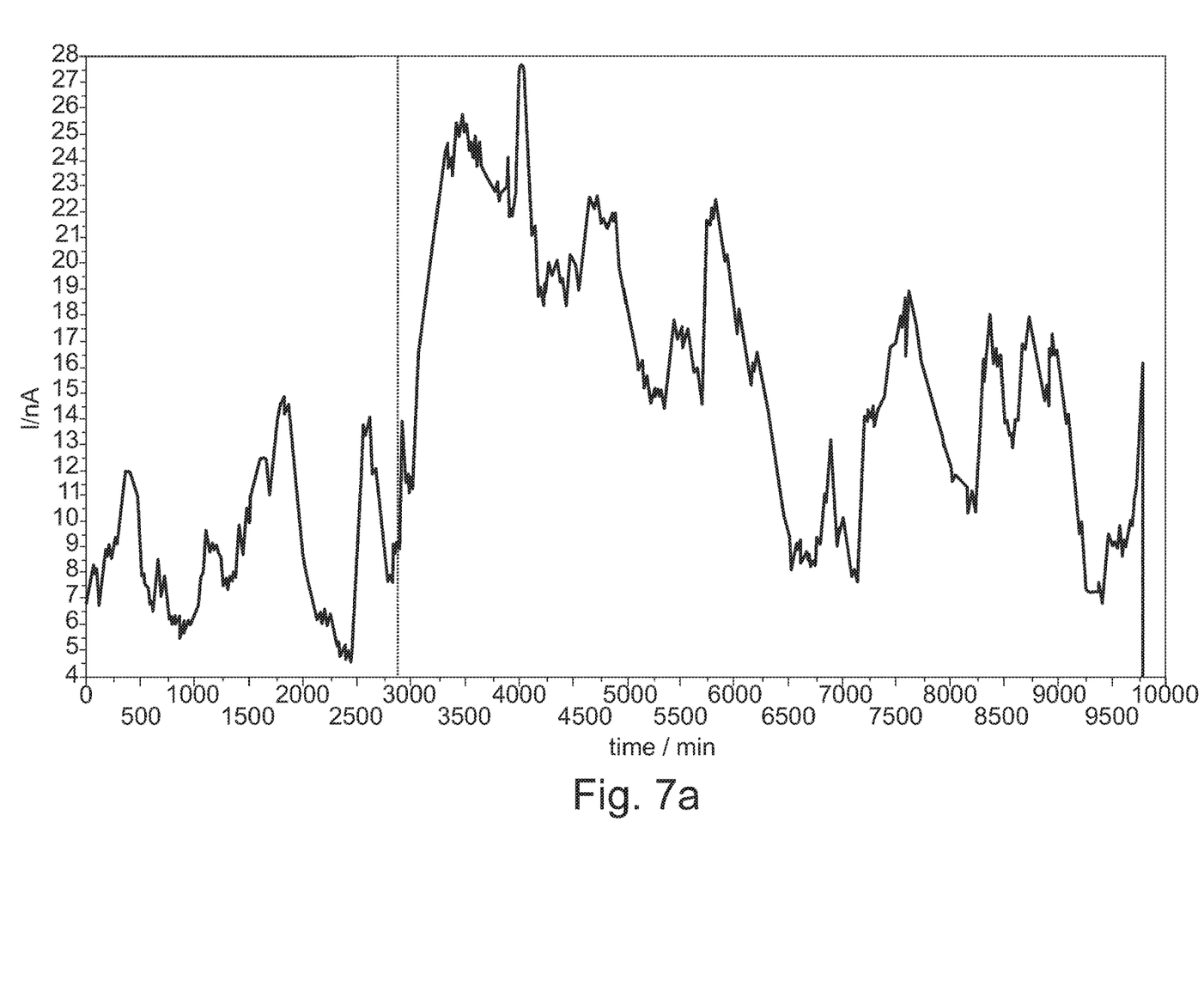
Figure 7B:
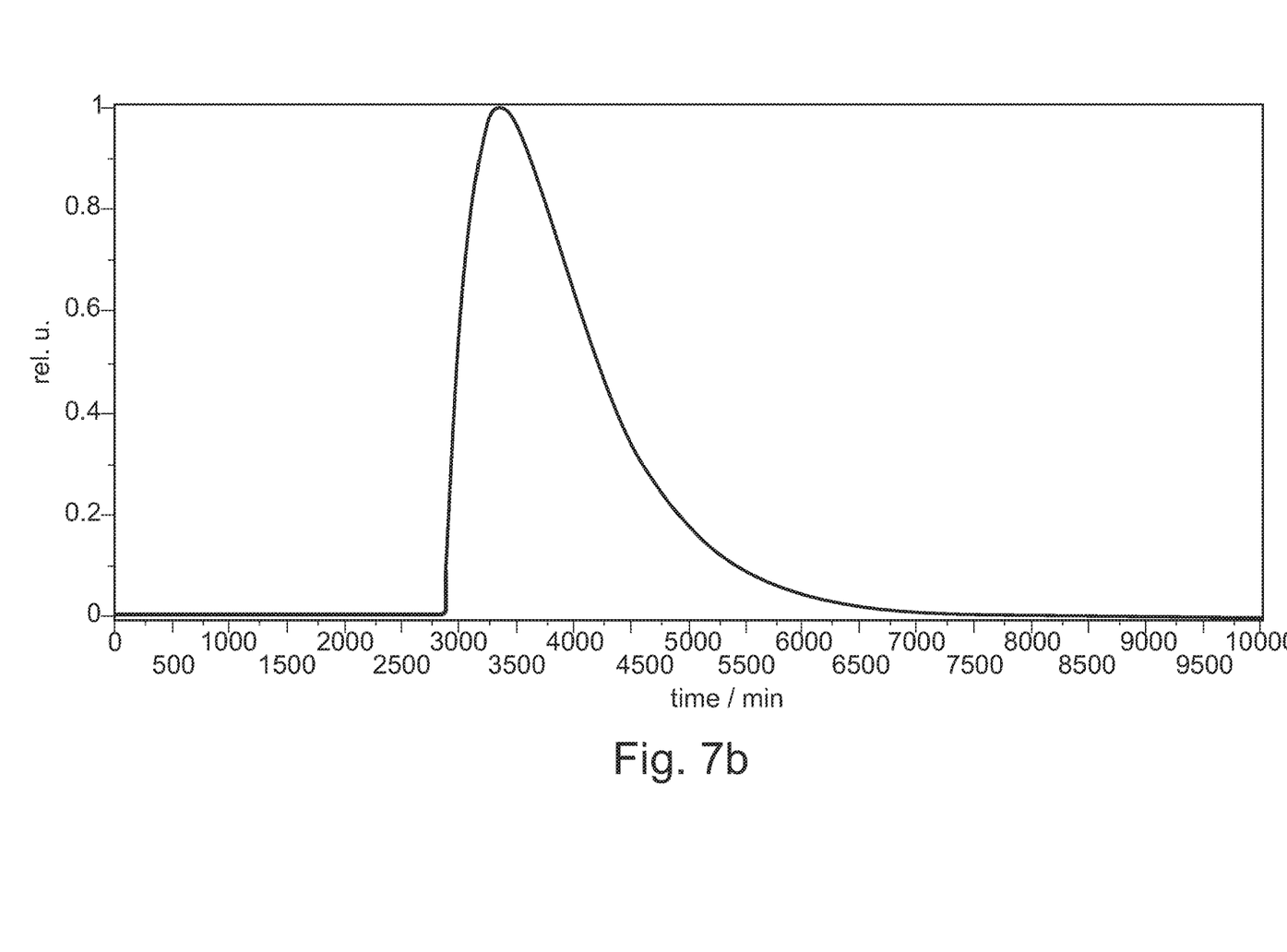

For the purpose of further explanation, FIGS. 7a to 7d show time depend signal curves derived from a simulation. Referring to FIG. 7a, a time dependent continuous sensor signal representing a signal of a glucose sensor, e.g. a current signal, is shown for which a signal interference started at a time of 2800 min. The simulated time dependence of the interfering signal is shown in FIG. 7b.

Figure 7C:
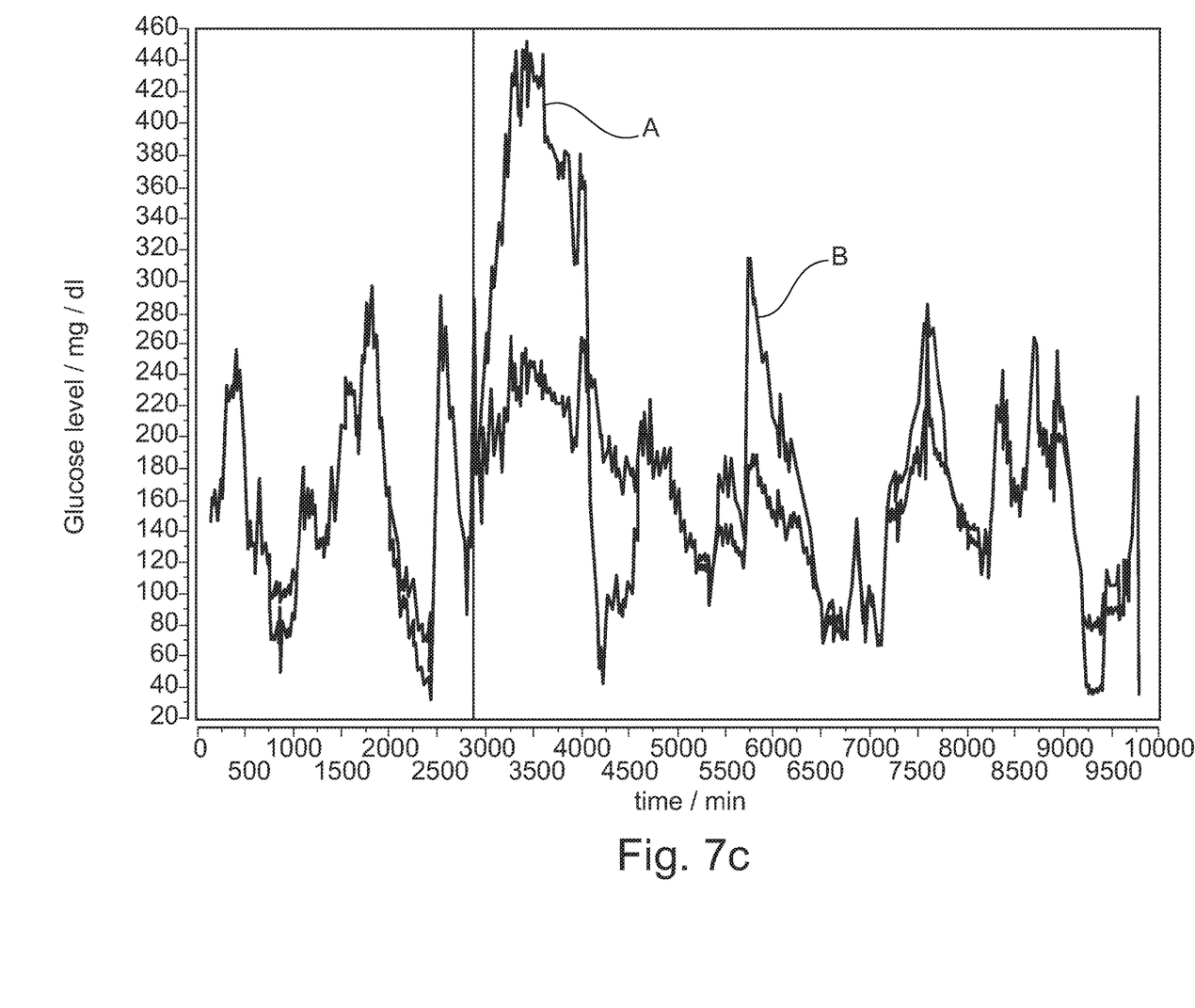
Figure 7D:
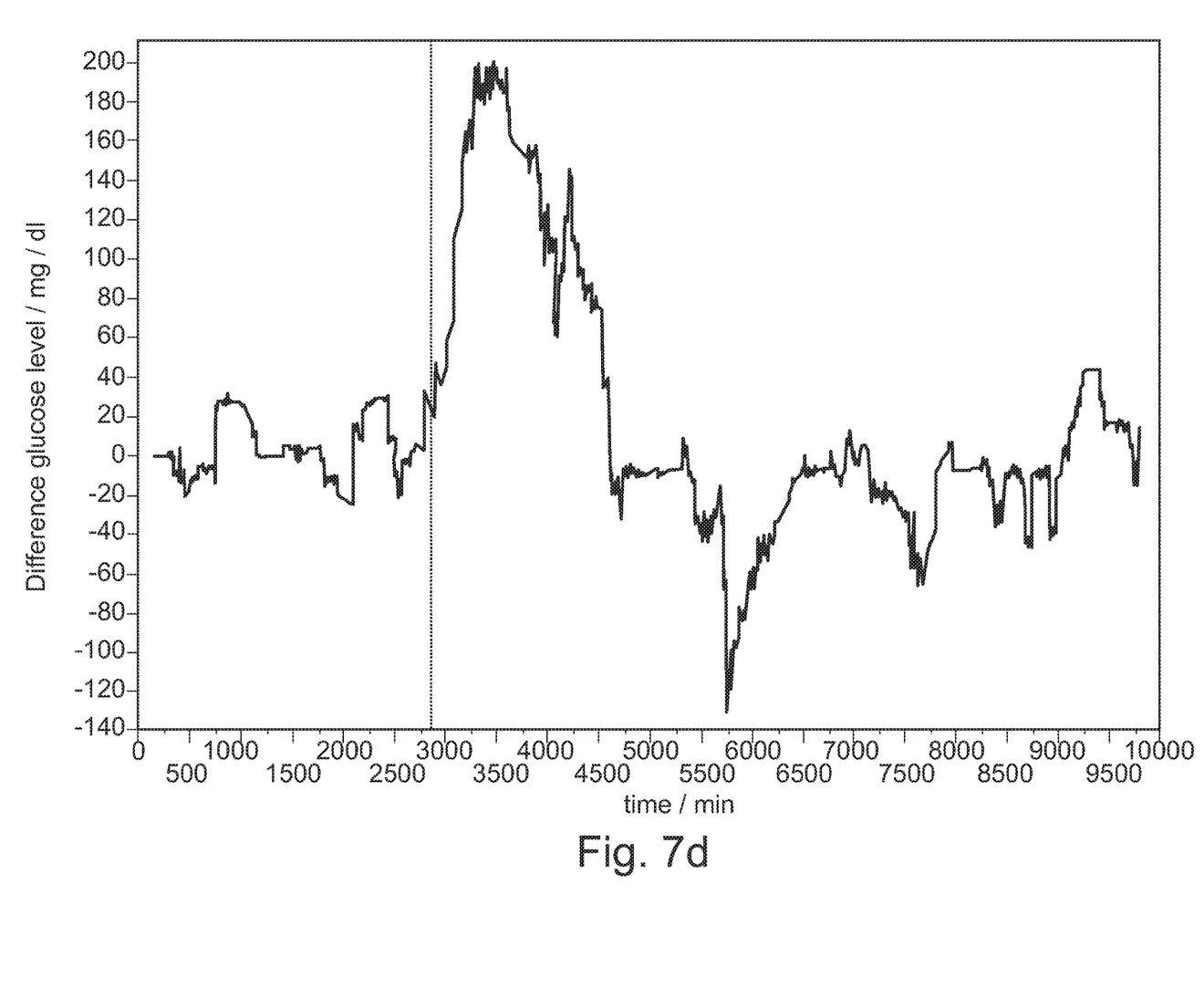

In FIG. 7c curve A represents a continuous glucose level without correction derived from the sensor signal curve in FIG. 7a. Curve B represents the corrected continuous glucose level derived by subtracting the interferent signal. Finally, FIG. 7d shows the difference between curve A and B in FIG. 7c. Such curve represents a pharmacokinetic course of the interferent composition in the body fluid under investigation. Within the noise level of the sensor element by which the signals are detected, FIG. 7d resembles the curve in FIG. 7b.

Figure 8:
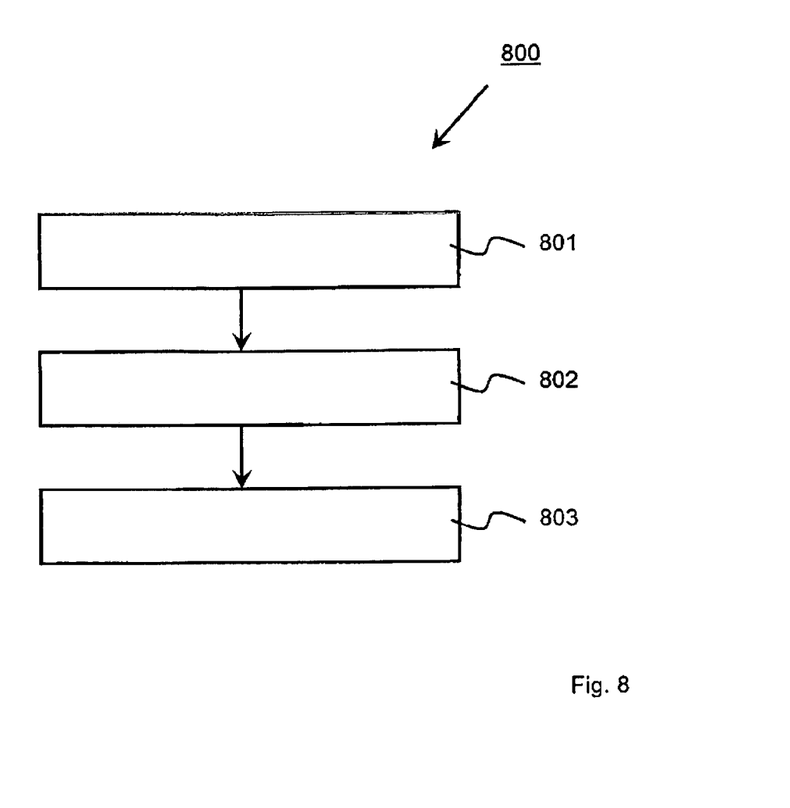

Referring to FIG. 8, an exemplary method 800 for determining a pharmacokinetic curve for an active substance or composition in a body fluid from a continuous sensor signal of a glucose sensor element of a continuous body fluid glucose monitoring device in a data processing unit is illustrated. The method 800 begins at step 801 where, in the processing unit, first measurement data are received, the first measurement data are representing a continuous sensor signal provided by a glucose sensor element of a continuous body fluid glucose monitoring device. The glucose sensor element may be configured for subcutaneous access. The data processing unit, for example, may be provided in the handheld diabetes management device 102 or the continuous glucose monitor 200. The processing module 404 or 502 may be provided with the data processing unit. The measurement data received are indicative of a continuous sensor signal provided by a glucose sensor element such as sensor 500.

In step 802, in the data processing unit, second measurement data are provided, the second measurement data representing a sensor signal provided from a further body fluid glucose monitoring different from the continuous body fluid glucose monitoring device. The further body fluid glucose monitoring may also be from the continuous body fluid glucose monitoring type. The first and second measurement data are processed for determining a pharmacokinetic curve of an active substance or composition causing time-dependent signal interference for the first measurement data. The second measurement data are not interfered by signal contribution of the active substance. Therefore, a pharmacokinetic curve can be determined from processing of the first and second measurement data (step 803). If the first and second measurement data represent the same glucose level of a patient, but measured independently, the pharmacokinetic curve may simply be determined by subtracting the second measurement from the first measurement data. Surprisingly, the measurements for determining body fluid glucose level may be used for determining kinetic behavior of an active substance or composition in the bodily fluid.

In general, the method 800 may also be performed by using measured data from a sensor element providing signals indicative of another analyte, such as lactate, present in the body fluid under investigation. The body fluid may be different from blood, e.g. urea or interstitial fluid. At least two independent measurements (measurement with the active component present; measurement with no presence of the active component) need to be analyzed. One or more steps of the method 800 may be combined with the method 600 or the system for determining the body fluid glucose level of a patient provided in the present disclosure. Also one or more steps of the method 600 or the system for determining the body fluid glucose level of a patient may be combined with the method 800 for determining the pharmacokinetic curve for an active substance or composition in a body fluid.

The invention claimed is:

1. A method for determining a body fluid glucose level of a patient, comprising:
   measuring, by a glucose sensor element of a continuous body fluid glucose monitoring device, a first glucose level of the patient and generating a first measurement data representing the first glucose level of the patient,
   receiving, in a data processing unit, the first measurement data from the continuous body fluid glucose monitoring device,
   receiving, in the data processing unit, a second measurement data representing a second glucose level of the patient provided by another glucose monitoring device,
   determining, by the data processing unit, a calibration signal by processing the first and second measurement data, the processing comprising subtraction of the second measurement data from the first measurement data, where the calibration signal embodies a presence of an interferent in a body fluid for which the body fluid glucose level is determined and a kinetic course of decomposition of the interferent in the body fluid, wherein the interferent is a substance different from glucose and the glucose sensor element is responsive to the interferent in the body fluid,
   receiving, by the data processing unit, a starting time of the presence of the interferent in the body fluid for which the body fluid glucose level is determined, wherein a calibration data includes the calibration signal and the starting time of the presence of the interferent,
   determining, by the data processing unit, the body fluid glucose level by processing subsequent first measurement data of the continuous body fluid glucose monitoring device and the calibration data, the processing of the subsequent first measurement data and the calibration data comprising subtraction of the calibration signal from the subsequent first measurement data of the continuous body fluid glucose monitoring device according to the starting time, and
   providing the determined body fluid glucose level as result data.

2. The method according to claim 1, further comprises generating a prompting signal to request receipt of the starting time.

3. The method according to claim 2, wherein the generating the prompting signal comprises receiving a user selection input.

4. The method according to claim 1, wherein the data processing unit is provided in one of a handheld body fluid glucose management device, and the continuous body fluid glucose monitoring device.

5. A system for determining a body fluid glucose level of a patient from a continuous sensor signal of a glucose sensor element of a continuous body fluid glucose monitoring device, comprising:
   the continuous body fluid glucose monitoring device; and
   a data processing device spatially distinct from the continuous body fluid glucose monitoring device and having:
   a processor; and
   a storage medium having computer program instructions stored thereon, wherein the computer program instructions, when executed by the processor, perform processing of:
   receive a measurement data representing the continuous sensor signal of the glucose sensor element of the continuous body fluid glucose monitoring device,
   receive a time-dependent zero-signal level of the glucose sensor element, wherein the time-dependent zero-signal level of the glucose sensor element embodies a presence of an interferent in a body fluid for which the body fluid glucose level is determined and a kinetic course of decomposition of the interferent in the body fluid, wherein the interferent is a substance different from glucose and the glucose sensor element is responsive to the interferent in the body fluid, wherein the time-dependent zero-signal level is stored in the storage medium,
   receive a starting time of the presence of the interferent in the body fluid for which the body fluid glucose level is determined,
   determine the body fluid glucose level by processing at least the measurement data, the time-dependent zero-signal level, and the starting time, the processing comprising subtraction of the time-dependent zero-signal level from the continuous sensor signal according to the starting time, and provide the determined body fluid glucose level as result data.

6. A method for determining a body fluid glucose level of a patient, comprising:
- measuring, by a glucose sensor element of a continuous body fluid glucose monitoring device, a pre-processed glucose level and generating a measurement data representing the pre-processed glucose level,
- receiving, in a data processing unit, the measurement data,
- receiving, by the data processing unit, a calibration signal for the glucose sensor element, where the calibration signal embodies a presence of an interferent in a body fluid for which the body fluid glucose level is determined and a kinetic course of decomposition of the interferent in the body fluid, wherein the interferent is a substance different from glucose and the glucose sensor element is responsive to the interferent in the body fluid,
- receiving, by the data processing unit, a starting time of the presence of the interferent in the body fluid for which the body fluid glucose level is determined, and
- determining, by the data processing unit, the body fluid glucose level by processing at least the measurement data, the calibration signal, and the starting time, the processing comprising subtraction of the calibration signal from the measurement data according to the starting time, and providing the determined glucose level as result data.

7. The method according to claim 6, further comprises generating a prompting signal to request receipt of the calibration signal and the starting time.

8. The method according to claim 7, wherein the generating the prompting signal comprises receiving a user selection input.

9. The method according to claim 6, wherein the data processing unit is provided in one of a handheld body fluid glucose management device, and the continuous body fluid glucose monitoring device.

* * * * *